United States Patent [19]
Osypka

[11] Patent Number: 5,954,742
[45] Date of Patent: Sep. 21, 1999

[54] DILATATION CATHETER

[76] Inventor: Peter Osypka, Basler Strasse 109, D-79639 Grenzach-Wyhlen, Germany

[21] Appl. No.: 08/818,574

[22] Filed: Mar. 14, 1997

[30] Foreign Application Priority Data

Mar. 16, 1996 [DE] Germany .......................... 196 10 461

[51] Int. Cl.⁶ .................................................. A61M 29/00
[52] U.S. Cl. .......................... 606/198; 606/194; 606/127; 606/201; 606/200; 604/48; 604/49
[58] Field of Search ..................................... 606/198, 194, 606/63, 191–192, 127, 201, 200; 604/48; 607/105, 122; 600/201, 204

[56] References Cited

U.S. PATENT DOCUMENTS

| | | |
|---|---|---|
| 3,557,794 | 1/1971 | Van Patten . |
| 4,808,163 | 2/1989 | Laub ........................................ 606/198 |
| 5,019,075 | 5/1991 | Spears et al. ................................ 606/7 |
| 5,336,178 | 8/1994 | Kaplan et al. ............................. 604/53 |
| 5,415,637 | 5/1995 | Khosravi .................................. 606/198 |

FOREIGN PATENT DOCUMENTS

| | | |
|---|---|---|
| 3516830 C2 | 7/1987 | Germany . |
| 9109006 U | 11/1991 | Germany . |
| WO91/01773 | 2/1991 | WIPO . |

Primary Examiner—Gary Jackson
Assistant Examiner—Lien Nao
Attorney, Agent, or Firm—Peter K. Kontler

[57] ABSTRACT

A balloon-free dilatation catheter has an elongated flexible sheath which is insertable into an animal body so that its distal end is located at or within a selected portion of an internal passage, such as in a blood vessel. The distal end normally confines an elongated cage-like expander having elongated at least partially resilient expanding elements which store energy when confined within the distal end but expand and bear against the tissue surrounding the selected portion of the internal passage when expelled from the distal end by one or more sleeve-like displacing elements confined in and movable circumferentially and/or longitudinally of the sheath. The expanding elements can carry one or more thermometers and/or the discharge end(s) of one or more conduits for a medication or another flowable substance and/or they can be connected to an energy source, e.g., to cool or heat and/or otherwise treat the tissue. The cage is configurated to effect a predictable expansion of a selected portion of an internal passage when it is expelled beyond the distal end of the sheath.

43 Claims, 5 Drawing Sheets

DILATATION CATHETER

BACKGROUND OF THE INVENTION

The invention relates to catheters in general, and more particularly to improvements in dilatation or expansion catheters which need not employ one or more inflatable and deflatable balloons. Still more particularly, the invention relates to improvements in dilatation catheters of the type wherein a mechanical dilator or expander is to be introduced into a selected portion of an internal passage or cavity in an animal body to act upon the tissue surrounding the selected portion of such passage or cavity (hereinafter called passage for short). By way of example, the catheter of the present invention can be utilized to dilate a constricted portion of a blood vessel.

U.S. Pat. No. 3,557,794 discloses a catheter wherein the expander or dilator comprises a set of leaf springs. A wire is attached to the ends of such springs and can be manipulated to change the shape of the springs by causing them to bulge outwardly and to thus expand a portion of an internal passage. A drawback of the patented catheter is that the expanding action of the leaf springs is neither predictable nor uniform because the extent of deformation (bulging, arching or bending) of each spring varies in the longitudinal direction of the expander. Thus, it can happen that the radially outermost portions of the deformed leaf springs bring about an excessive expansion of the corresponding portion of an internal passage but the immediately adjacent portions of such passage are subjected to a much less pronounced (and normally much less satisfactory) expanding action or no dilatation at all.

Attempts to overcome the drawbacks of the patented catheter include the utilization of catheters which employ inflatable balloons. For example if the inflated balloon at the distal end of a balloon-introducing sheath assumes a substantially cylindrical shape, it is capable of effecting a more or less uniform expansion of tissue surrounding a selected portion of an internal passage, such as that defined by a blood vessel. However, balloon catheters exhibit the drawback that, as long as the balloons are inflated, they normally or invariably prevent the flow of a body fluid through the expanded portion of a blood vessel or the like. Presently known attempts to avoid the just outlined drawbacks of balloon catheters contribute significantly to their cost but do not invariably ensure an uninterrupted flow of blood and/or another fluid through the balloon-dilated portion of an internal passage.

Cardiologists and radiologists are frequently required to ensure that a selected portion of an internal passage remains open (unobstructed), at least for a certain interval of time. For example, such temporary preventing of obstruction (i.e., temporary retention of a selected portion of an internal passage in a fully or at least adequately expanded condition) is often necessary in order to prevent spasmodic contraction of an artery during balloon angioplasty. Thus, at least under certain circumstances, the artery must be maintained in an expanded condition during angioplasty in order to prevent certain parts of the intima from causing or entailing contraction of the artery not unlike the closing of a valve. Such spasmodic contraction can be remedied or counteracted only by resorting to undertakings as drastic as bypass surgery. This can be avoided by reliably ensuring an at least temporary flow of blood to various parts of an animal body, e.g., to certain vessels of the heart, at a required or optimum rate.

Furthermore, a satisfactory carrying out of angioplasty often necessitates or renders it desirable to subject the tissue surrounding a selected portion of an internal passage to a particular treatment subsequent to completion of balloon dilatation; this reduces the risk of renewed stenosis.

OBJECTS OF THE INVENTION

An object of the invention is to provide a novel and improved dilatation catheter which is constructed and assembled in such a way that it permits and ensures a highly predictable expansion of selected portions of tissue surrounding an internal passage in a human or other animal body.

Another object of the invention is to provide a dilatation catheter which is less likely to subject selected portions of human or other animal tissue to excessive or insufficient expansion than heretofore known dilatation catheters.

A further object of the invention is to provide a novel and improved mechanical expander or dilator for use in the above outlined catheter.

An additional object of the invention is to provide the catheter with novel and improved means for moving the expander relative to an elongated flexible sheath which is used to introduce the expander into a selected portion of an internal passage, such as into a selected portion of a blood vessel.

Still another object of the invention is to provide a novel and improved method of dilating selected portions of internal passages by resorting to a dilatation catheter of the above outlined character.

A further object of the invention is to provide the above outlined catheter with a versatile expander or dilator which, in addition to mechanically expanding selected portions of internal passages, can perform one or more additional important functions, such as furnishing information concerning the temperature in a selected portion of an internal passage, heating and/or cooling and/or otherwise treating the tissue surrounding an expanded portion of an internal passage, and/or supplying one or more medications or other flowable substances to tissue surrounding a selected portion of an internal passage.

Another object of the invention is to provide a dilatation catheter which can be readily converted for the expansion of larger or smaller portions of internal passages by the simple and time-saving expedient of replacing a particular expander or dilator with a different expander or dilator.

An additional object of the invention is to provide the improved catheter with a set of spare expanders to enable the physician in charge to select the extent of expansion and/or the dimensions of that portion of an internal passage which requires expansion to an accurately determined extent.

Still another object of the invention is to provide a relatively simple, inexpensive and compact dilatation catheter which can be utilized as a superior substitute for presently known balloon catheters or ballon-free catheters.

Another object of the invention is to provide a versatile balloon-free dilatation catheter which can be utilized with advantage in connection with a variety of different treatments of tissue surrounding selected portions of blood vessels and/or other types of internal passages in human and/or other animal bodies.

SUMMARY OF THE INVENTION

The invention resides in the provision of a catheter for the treatment (such as heating, cooling, contacting with a flowable substance and/or mechanical dilatation) of tissue surrounding a passage in a portion of an animal body, e.g., in a blood vessel. The improved catheter comprises an elongated flexible tubular sheath having a distal end adapted to be introduced (in a manner not forming part of the present invention) into a selected portion of a passage, and an expander or dilator including a plurality of at least partially resilient expanding elements together defining a cage-like receptacle (hereinafter called cage for short) which is contractible and expandible radially of the tubular sheath between a contracted condition within and a radially expanded condition outside of the distal end of the sheath. The expanding elements have spaced apart distal and proximal terminals and at least substantially parallel elongated intermediate sections between the respective distal and proximal terminals. The elements are maintained in a stressed condition when located within the sheath, and such elements tend to expand radially outwardly beyond the distal end of the sheath to bear upon the tissue surrounding the selected portion of a passage when at least the distal terminals and the intermediate sections are located outside of the distal end of the sheath. The catheter further comprises means for moving the expanding elements of the expander or dilator within, beyond and back into the distal end of the sheath.

The expander is preferably designed in such a way that its proximal and distal terminals respectively define first and second annular sections having at least substantially unchanging diameters. That portion of the cage which includes the intermediate sections of the expanding elements is preferably dimensioned in such a way that its diameter exceeds the substantially unchanging diameters of the two annular sections when the intermediate sections are located outside of the distal end of the sheath as a result of movement of the distal terminals and the intermediate sections beyond the distal end of the sheath. The extent to which the diameter of the aforementioned portion of the cage then exceeds the unchanging diameters of the two annular sections is determined by the extent of stress upon the expanding elements when their intermediate sections are located within the sheath as well as upon the resistance offered by the tisue which surrounds the selected portion of a passage when at least the distal terminals and the intermediate sections of the expanding elements are located outside and at the distal end of the sheath.

The intermediate section of each expanding element can include or can constitute at least one wire-like body, such as a filament consisting of or containing a metallic or plastic material. The intermediate sections of the expanding elements are or can be at least substantially straight, and they can together constitute an elongated substantially tubular portion of the cage. Such tubular portion of the cage can resemble or it can constitute a cylinder, at least when the intermediate sections and the distal terminals of the expanding elements are located outside of the distal end of the sheath.

In accordance with a presently preferred embodiment, the intermediate sections of the expanding elements together form an elongated hollow cylindrical envelope, at least when they are located outside of the sheath, and the envelope contains a plurality of at least substantially straight wire-like components which are at least substantially parallel to the longitudinal axis of the cylindrical envelope.

The expander can further comprise a tubular follower which is connected with and extends beyond the distal terminals of the expanding elements in a direction away from the intermediate sections of such elements. Such catheter preferably further comprises an elongated flexible guide (e.g., a length of wire) which is surrounded by the sheath and by the follower and includes a normally exposed proximal end portion adjacent the proximal end of the sheath and a normally exposed distal end portion adjacent the follower.

The means for moving the expander relative to the sheath can include an elongated tube having a distal end portion associated with (e.g., welded or otherwise bonded to) the proximal terminals of the expanding elements and extending within an annulus which is defined by the proximal terminals of the elongated expanding elements, as well as toward the proximal end of the sheath. Such tube can contain or it can consist of a metallic material. The distal end portion of the tube is preferably secured to the proximal terminals of the expanding elements in such a way that it maintains the proximal terminals in mutual positions in which the proximal terminals together form an annulus adjacent the intermediate sections of the expanding elements. As mentioned above, the distal end portion of the tube can be bonded (such as welded or soldered or glued) to the proximal terminals of the expanding elements. The arrangement can be such that the proximal terminals of the expanding elements are adjacent the external surface of the distal portion of the tube.

The moving means including the above discussed elongated tube can further comprise an elongated flexible displacing member which is affixed to the tube and extends within and at least to the proximal end of the sheath. The displacing member can be affixed to the proximal end portion of the tube, and such proximal end portion preferably extends beyond the proximal terminals of the expanding elements in a direction toward the proximal end of the sheath.

The displacing member can constitute an elongated flexible sleeve which is disposed in the sheath and is at least indirectly (such as by way of the aforementioned tube) connected with the proximal terminals of the expanding elements. This displacing member is preferably designed to stand compressive as well as tensional stresses when it is confined in the sheath so that it can pull or push the proximal terminals of the expanding elements relative to the sheath.

The moving means including the aforementioned tube and/or the aforementioned displacing member preferably further comprises a handgrip portion which is affixed to the proximal end portion of the displacing member and is accessible at the proximal end of the sheath to facilitate a longitudinal shifting of the displacing member and of the proximal terminals of the shifting elements relative to the sheath. The displacing member and the handgrip portion can be said to jointly constitute a means or device for imparting to the proximal terminals of the expanding elements at least one of a plurality of movements including longitudinally and circumferentially of the sheath, i.e., to turn the expander relative to the distal end of the sheath and/or to impart to the expander a translatory movement in the longitudinal direction of the sheath.

In accordance with a presently preferred embodiment of the invention, the means for moving the expander relative to the sheath comprises a first substantially sleeve-like displacing member which is disposed within the sheath and is at least indirectly connected with the proximal terminals of the expanding elements (such as by means of the aforementioned tube), and a second substantially sleeve-like displacing member which is disposed within the sheath and is at least indirectly connected to the proximal terminals of the expanding elements. One of the displacing members is or can be surrounded by the other displacing member, and at least one of these displacing members is preferably movable relative to the other displacing member at least in one of a plurality of directions including longitudinally and circumferentially of the sheath. Such presently preferred moving means can further comprise at least one handgrip member which is accessible at the proximal end of the sheath and is connected to at least one of the displacing members. The at least one handgrip member can be affixed to each of the first and second displacing members for movement relative to the proximal end of the sheath at least in one of a plurality of directions including longitudinally and circumferentially of the sheath.

If the expander includes the aforementioned follower which is affixed to the distal terminals of the expanding elements, and if the means for moving the expander relative to the sheath comprises at least one elongated sleeve-like displacing member which is (directly or indirectly) affixed to the aforesaid proximal terminals of the expanding elements, the aforementioned elongated flexible guide extends through the follower and through the at least one displacing member. The guide is movable relative to the displacing member and relative to the follower (and/or vice versa) in at least one of the directions longitudinally and circumferentially of the sheath.

The expander can include an array of between three or four and ten expanding elements, e.g., six expanding elements having straight parallel intermediate sections which are equidistant from each other in the circumferential direction of the sheath.

The catheter can further comprise a thermometer which is associated with at least one of the expanding elements; for example, the catheter can comprise a discrete thermometer for each expanding element. If two or more thermometers are employed, they can be affixed to the intermediate sections of the respective expanding elements and can be staggered relative to each other in the longitudinal direction of the cage, i.e., in a direction from the proximal toward the distal terminals of the expanding elements.

The catheter can further comprise (or it can be utilized in conjunction with) a source of energy, such as high-frequency energy, and the catheter then also includes means for connecting such energy source with at least one of the expanding elements. The connecting means can comprise a tubular conductor which is connected to one or more expanding elements of the expander. If the catheter further comprises a thermometer for each of the expanding elements, or a thermometer for a single expanding element or thermometers for two but less than all of the expanding elements, the single thermometer or each of two or more thermometers can occupy a preselected position as seen in the longitudinal direction of the cage; for example and as already mentioned above, if the catheter comprises two or more thermometers, such plural thermometers can be staggered relative to each other in the longitudinal direction of the cage and of the sheath.

If the means for moving the expander includes elongated tubular sleeve-like displacing members which are fitted into each other, if the catheter comprises one or more thermometers carried by one or more expanding elements, and if the catheter further comprises means for connecting an energy source with one or more expanding elements, the conductor or conductors leading from the thermometer or thermometers to the proximal end of the sheath and/or one or more conductors constituting the aforementioned connecting means can extend from the expander to the proximal end of the sheath between the two interfitted sleeve-like displacing members.

The distal terminals of the expanding elements can be disposed in or adjacent a first plane, and the proximal terminals of such expanding elements can be located in or adjacent a second plane. Such planes can but need not be parallel to each other, at least one of these planes can include the respective tips or extremities of the intermediate sections and can be normal to the longitudinal axis of the sheath, at least one of these planes and the axis of the sheath can make an oblique angle, or the tips or extremities of the intermediate sections can form a hollow cone or pyramid adjacent the respective annulus of (proximal or distal) terminals.

The improved dilatation catheter can further comprise means for conveying a flowable substance (such as a liquid medication) from the proximal end of the sheath, within the sheath, and to at least one of the expanding elements. The conveying means can include a portion which forms part of the at least one expanding element; for example, at least a portion of the at least one expanding element can constitute a conduit (such as a hose) for the flowable substance (which can be a readily flowable liquid or of a more viscous consistency). Such conduit can have at least one outlet for the flowable substance, and this at least one outlet can be positioned and configurated and oriented to discharge flowable substance substantially radially of and away from an elongated axis of the cage. It is also possible to utilize conveying means including at least one conduit (such as an elastic hose) which surrounds the at least one expanding element and has a discharge end for the flowable substance at the intermediate section of the respective expanding element.

The novel features which are considered as characteristic of the invention are set forth in particular in the appended claims. The improved dilatation catheter itself, however, both as to its construction and the mode of assembling and utilizing the same, together with numerous additional important and advantageous features thereof, will be best understood upon perusal of the following detailed description of certain presently preferred specific embodiments with reference to the accompanying drawings.

DESCRIPTION OF PREFERRED EMBODIMENTS

Figure 1:
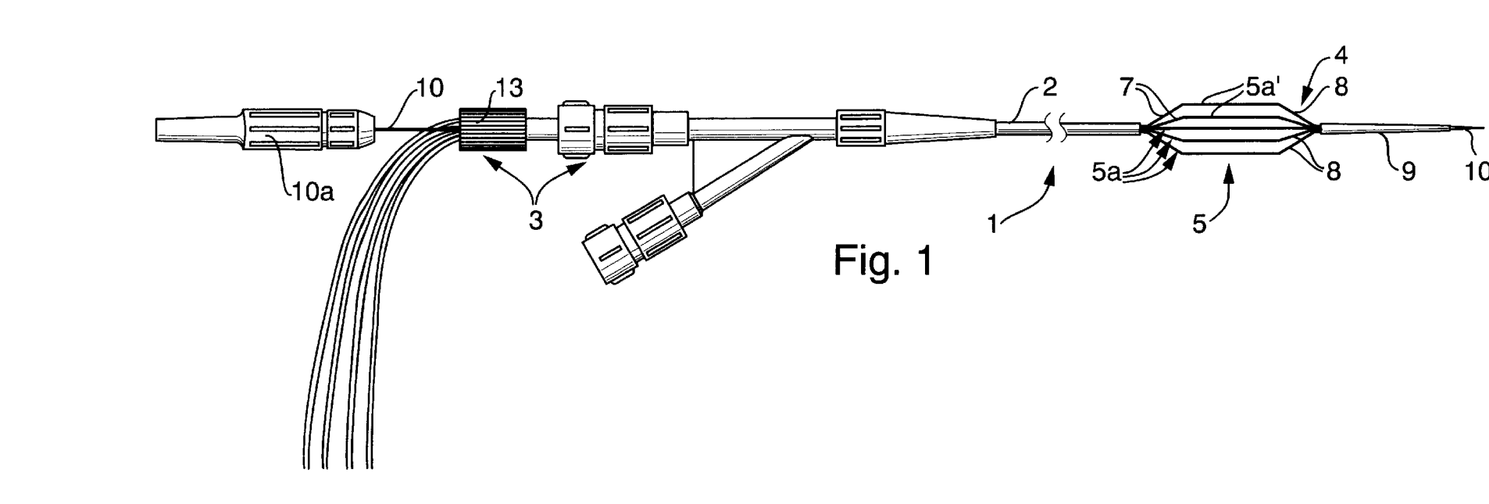
FIG. 1 is a fragmentary schematic elevational view of a dilatation catheter which embodies one form of the invention, the cage of the expander being shown in the expanded condition outwardly adjacent the distal end of the sheath.
Figure 2:
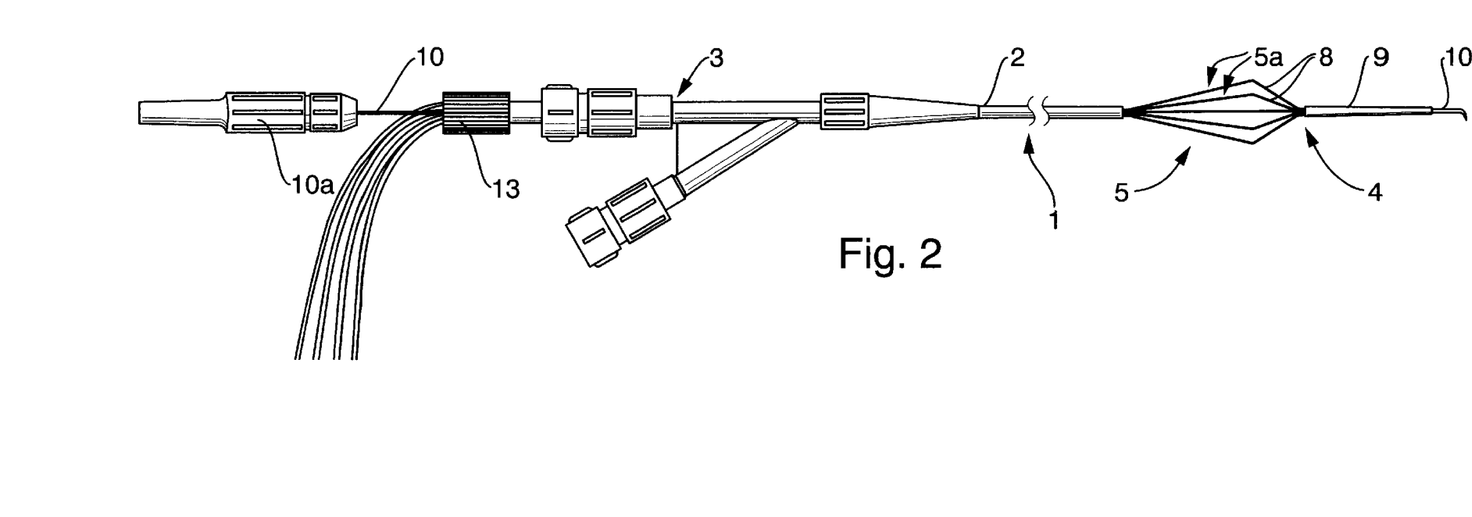
FIG. 2 illustrates the structure of FIG. 1 but with the cage of the expander partially retracted into the distal end of the sheath.
Figure 3:
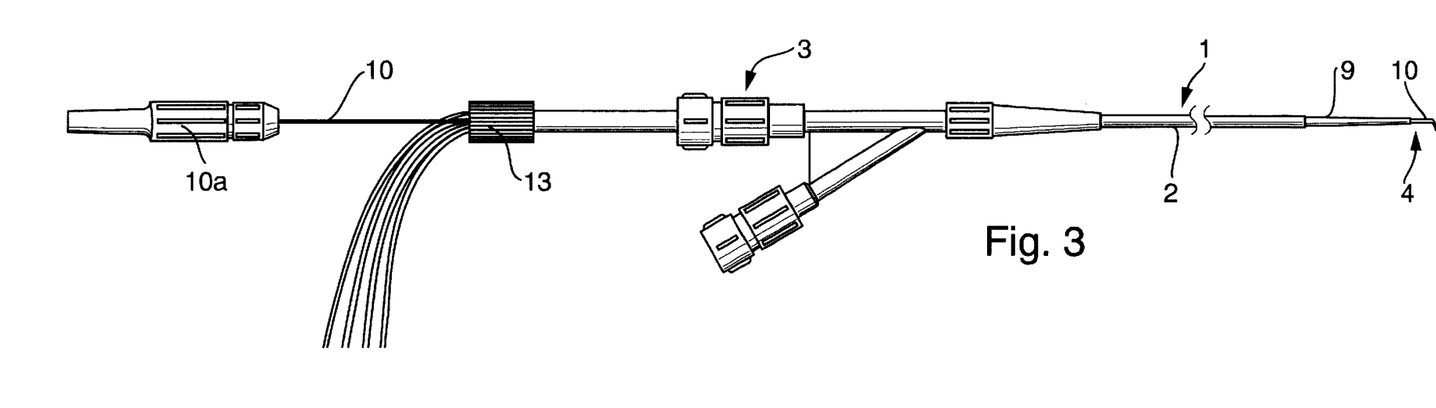
FIG. 3 illustrates the structure of FIG. 2 but with the cage of the expander fully confined in the distal end of the sheath.

Referring first to FIG. 1, there is shown a dilatation catheter 1 comprising an elongated flexible tubular sheath 2 of plastic or other suitable material and having a proximal or manipulating end 3 and a distal or working end 4. The catheter 1 further comprises a novel and improved expander or dilator 5 which is movable at least in the longitudinal direction of the sheath 2 between a fully exposed (and hence at least partially expanded) position or condition shown in FIG. 1 (in which the expander 5 is outwardly adjacent the distal end 4 of the sheath 2), a partially retracted or collapsed condition shown in FIG. 2 (in which a portion of the expander 5 is already or still confined in the distal end 4 of the sheath 2), and a fully collapsed or concealed condition or position which is shown in FIG. 3 and in which the expander 5 is fully confined or concealed in the distal end 4.

Figure 8:
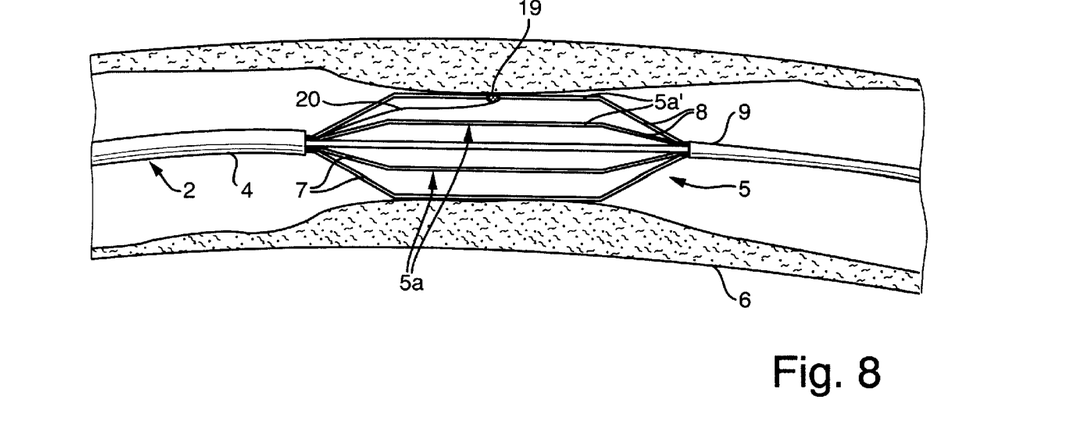
FIG. 8 shows the structure of FIG. 6 but with the guide for the follower of the expander partially retracted and with the cage of the expander located within a narrowed portion of an internal passage defined by a blood vessel.

When the expander 5 is confined in the distal end 4 of the sheath 2, its elongated expanding elements 5a are caused to store energy which is dissipated, to a desired extent, when the expander is moved outwardly and beyond the distal end 4, e.g., to the position which is shown in FIG. 8 and in which the resilient elongated central portions or sections 5a' of its elements 5a bear against the tissue surrounding a selected (e.g., constricted) portion of a passage defined by a portion (such as a blood vessel 6) of an animal (such as human) body. The force with which the sections 5a' bear against the surrounding tissue depends upon the dimensions of the constriction in the vessel 6 and upon the amount of energy stored in the expander 5 when the sections 5a' of its expanding elements 5a are confined in the distal end 4 of the sheath 2.

Figure 6:
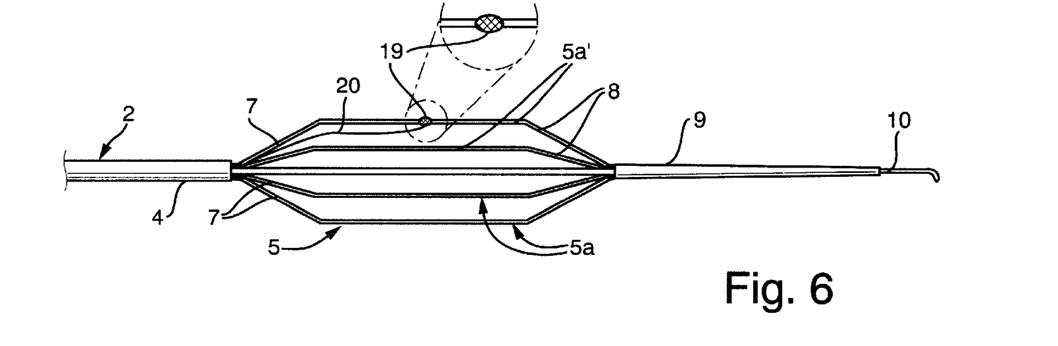
FIG. 6 is an enlarged view of the right-hand portion of the catheter which is shown in FIG. 1, and further showing a thermometer and a conductor extending from the thermometer toward the proximal end of the sheath.
Figure 7:
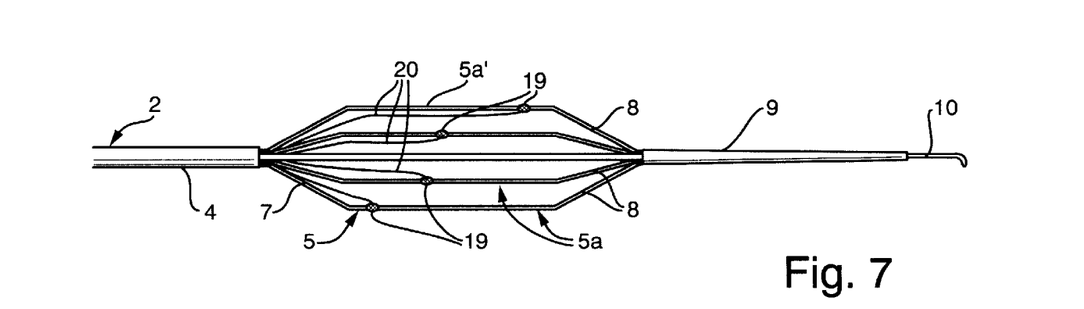
FIG. 7 is a view similar to that of FIG. 6 but showing several thermometers, each affixed to a discrete expanding element, and a corresponding number of conductors extending from the thermometers toward the proximal end of the sheath.

As can be seen, for example, in FIGS. 6, 7 and 8, the expander or dilator 5 forms an elongated at least substantially cylindrical cage surrounded by straight elongated sections 5a' of the expanding elements 5a, and the sections 5a' are at least substantially parallel to each other and to the central longitudinal axis of the cage. The proximal terminals 7 of the expanding elements 5a are disposed in a first plane which is or which can be normal to the longitudinal axis of the adjacent portion (distal end) 4 of the sheath 2, and the same holds true for the common plane of the distal terminals 8 of the elements 5a.

The expander 5 further comprises an elongated tubular follower 9 which is welded, glued or otherwise secured or affixed to the distal terminals 8 and surrounds a portion of an elongated wire-like or rope-like guide 10 having a distal end portion extending beyond the follower 9 at least when the expander 5 is collapsed and confined in the distal end 4 of the sheath 2. As can be seen in FIG. 1, the proximal end portion of the guide 10 is accessible and is provided with a suitable handgrip portion or handgrip member 10a at the proximal end 3 of the sheath 2. The entire sheath 2 can be moved (by a handgrip portion or handgrip member 13 relative to the guide 10 and/or vice versa.

The distal end 4 of the sheath 2 is introduced into a selected portion of an internal passage (e.g., in the blood vessel 6) while the expander 5 is confined in the distal end 4 (see FIG. 3). The person in charge then proceeds to manipulate the handgrip portion 13 of a mechanism or system (including coaxial sleeve-like flexible displacing members 12 and 14) which serves to move the expander 5 in the circumferential and/or longitudinal direction of the sheath 2 so that the expander becomes exposed and its elements 5a can dissipate certain amounts of energy (see FIG. 8) to bear upon the surrounding tissue. The amount of energy which can be stored in the collapsed (confined) expander 5 can be selected within a desired range by supplying the catheter 1 with a given number of spare expanders 5 and moving means (11 to 14) therefor. The expander 5 will assume the intermediate stage of partial expansion (as shown in FIG. 2) during expulsion from as well as during retraction into the distal end 4 of the sheath 2.

It is clear that the improved catheter 1 can be utilized to bring about an initial expansion of a selected portion of an internal passage as well as to prevent premature (if any) narrowing of a selected portion of an internal passage subsequent to an initial expansion by the improved catheter or by any other suitable or available means.

The elements 5a of the expander 5 can be made of a metallic or other suitable (such as plastic) wire. The illustrated elongated cylindrical shape of the cage defined by the exposed expander 5 is the presently preferred shape; however, it is equally within the purview of the invention to assemble and configurate the elements 5a in such a way that the cage can resemble an at least slightly truncated pyramid or cone or a twin pyramid or cone (or any other advantageous or necessary configuration). The elongated central sections 5a' of the expanding elements 5a extend in at least substantial parallelism with the imaginary axis of the cage which is shown in FIG. 1, 6, 7 or 8, and these sections are preferably equidistant from each other as seen in a circumferential direction of the distal end 4.

When the catheter 1 is to be introduced into a vessel 6 or the like, the guide 10 is introduced in a first step, and the components 2, 5 and 11–14 of the catheter are introduced (along the already inserted guide 10) in a next-following step. It will be seen that the guide 10 can be considered to constitute a component part which is distinct from the actual catheter 1 or as a constituent of such catheter.

Figure 4:
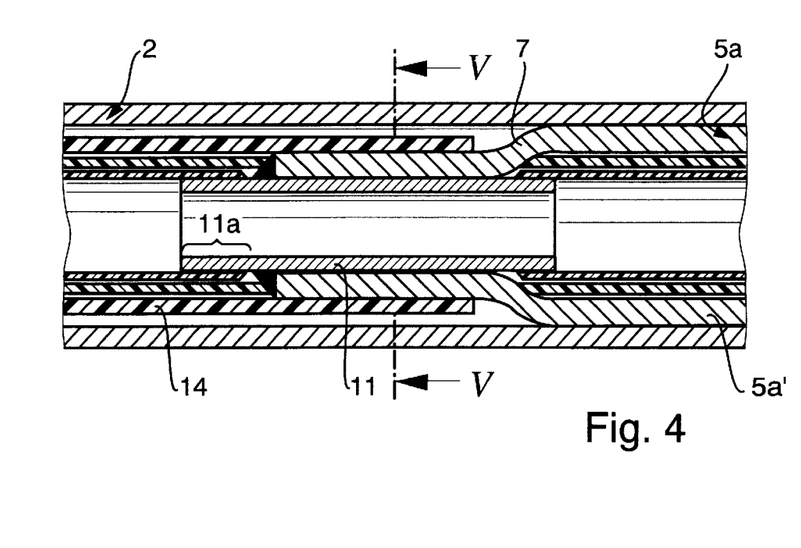
FIG. 4 is a greatly enlarged axial sectional view of the distal end of the sheath, of a portion of the expander in the contracted condition within the distal end, and of a portion of the means for moving the expander longitudinally and/or circumferentially of the sheath.
Figure 5:
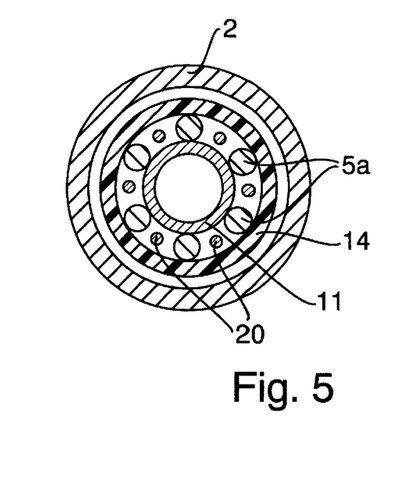
FIG. 5 is a transverse sectional view substantially as seen in the direction of arrows from the line V–V in FIG. 4.

The means for moving the expander 5 relative to the sheath 2 further comprises a preferably metallic tube or sleeve 11 having a distal end portion which is welded, soldered or otherwise bonded or secured to the elements 5a of the expander 5. Reference may be had to FIGS. 4 and 5 which show the expander, the adjacent distal end 4 of the sheath 2 and the parts of the moving means in greatly enlarged longitudinal and transverse sectional views. The tube 11 can be utilized to move the expander 5 longitudinally of the distal end 4 as well as to change the angular position of the expander 5 relative to the sheath 2 while the expander is confined in or is outwardly adjacent the distal end 4. The aforementioned elongated sleeve-like displacing members 12, 14 and the handgrip portion or member 13 serve as a means for moving the tube 11 (and hence the expander 5) angularly and/or longitudinally of the sheath 2.

The proximal terminals 7 of the expanding elements 5a are adjacent the external surface of the tube 11 and are secured (e.g., welded) thereto. The proximal end portion 11a of the tube 11 extends beyond the proximal terminals 7 in a direction toward the proximal end 3 of the sheath 2. The distal end portion of the sleeve-like displacing member 12 surrounds and is affixed to the proximal end portion 11a of the tube 11 so that the member 12(which is designed to predictably push or pull the tube 11 in the sheath 2) can move the expander 5 relative to the sheath 2 and guide 10 in any one of several directions and to a desired extent. The proximal end portion of the displacing member 12 (this member is confined in the sheath 2 and surrounds the guide 10) is affixed to and can be turned and/or longitudinally moved by the aforementioned handgrip portion or handgrip member 13 which is outwardly adjacent the proximal end 3 of the sheath 2. Once the expander 5 is exposed adjacent the distal end 4 of the sheath 2, the handgrip portion 13 can be used to impart a smoothing and/or other action to the tissue surrounding the constricted portion of the vessel 6 by causing the cage including the elongated sections 5a' to move relative to such tissue in the longitudinal direction of the vessel 6 and/or to turn in the vessel 6.

FIGS. 4 and 5 further show that the proximal terminals 7 of the expanding elements 5a are confined in and secured to the distal end portion of the second elongated. sleeve-like displacing member 14 of the means for moving the expander 5 relative to the distal end 4 of the sheath 2. The member 14 surrounds the member 12 and its proximal end portion is or can be affixed to and moved by the handgrip portion or handgrip member 13 which is secured to the proximal end portion of the member 12. The proximal terminals 7 of the elements 5a can be glued to the internal surface of the distal end portion of the member 14 in such a way (see FIG. 5) that they are at least substantially equidistant from each other (as. seen in the circumferential direction of the proximal end portion 11a of the tube 11).

The forces which are applied to and which tend to turn and/or to move the handgrip portion 13 longitudinally relative to the sheath 2 are transmitted to the displacing members 12, 14 which, in turn, displace the tube 11 and hence the expander 5 accordingly. The ability of the members 12, 14 to transmit forces to the tube 11 and to the expander 5 is or can be selected in such a way that the sections 5a' of the expanding elements 5a can move relative to the tissue surrounding the selected portion of the passage in the vessel 6 even though the sections 5a' bear upon such tissue with a certain force determined by the amount of energy still stored in the elements 5a of the exposed or expelled expander 5 and by the diameter of the respective portion of the internal passage.

The distal terminals 8 of the expanding elements 5a are affixed to the tubular follower 9 of the expander 5. The inner diameters of the tube 11 and of the follower 9 exceed the diameter of the wire-like guide 10 so that the latter can readily turn within and/or move longitudinally of the parts 9, 11 and/or vice versa. This can be seen, for example, in FIGS. 1, 6 and 7. The guide 10 has been omitted in FIGS. 4 and 5 for the sake of clarity.

The number of expanding elements 5a can vary within a rather wide range, for example, between three or four and ten to twelve. As shown in FIG. 5, a presently preferred expander 5 comprises six elongated wire-like or filament-like resilient expanding elements 5a which are equidistant from each other as seen in the circumferential direction of the distal end 4 of the sheath 2. It has been found that an expander with six equidistant elements 5a can quite reliably and repeatedly expand a selected portion of an internal passage and can be assembled and installed in the catheter at an acceptable cost. The number of elements 5a is preferably limited to a minmu acceptable number because this reduces the bulk of the expander, a feature which is highly important in dilatation catheters. Thus, one will normally select a number of expanding elements 5a which suffices to ensure the establishment of a satisfactory elongated cylindrical or otherwise configured cage while also ensuring that the collapsed expander 5 will fit into a distal end 4 having a relatively small inner diameter.

An important advantage of the improved catheter 1 is that, when it is permitted to expand adjacent the distal end 4, the expander can ensure a predictable (practically unrestricted) flow of a body fluid (e.g., blood) in a vessel 6, i.e., a flow at a desired optimum obtainable or achievable rate or as close to such optimum rate as possible. The energy which is stored in the expanding elements 5a can be selected in such a way that the exposed expander 5 can actually dilate a selected portion of an internal passage to a noticeable extent or that it merely (more or less) prevents further contraction (narrowing) of such selected portion.

The improved catheter can also serve as a means for subjecting the tissue surrounding an internal passage to a number of treatments other than a purely mechanical (expanding, smoothing and or massaging) treatment. For example, the catheter can be used to prevent a recurrence of stenosis by subjecting the tissue to a densifying, smoothing and/or thermal treatment.

Figure 9:
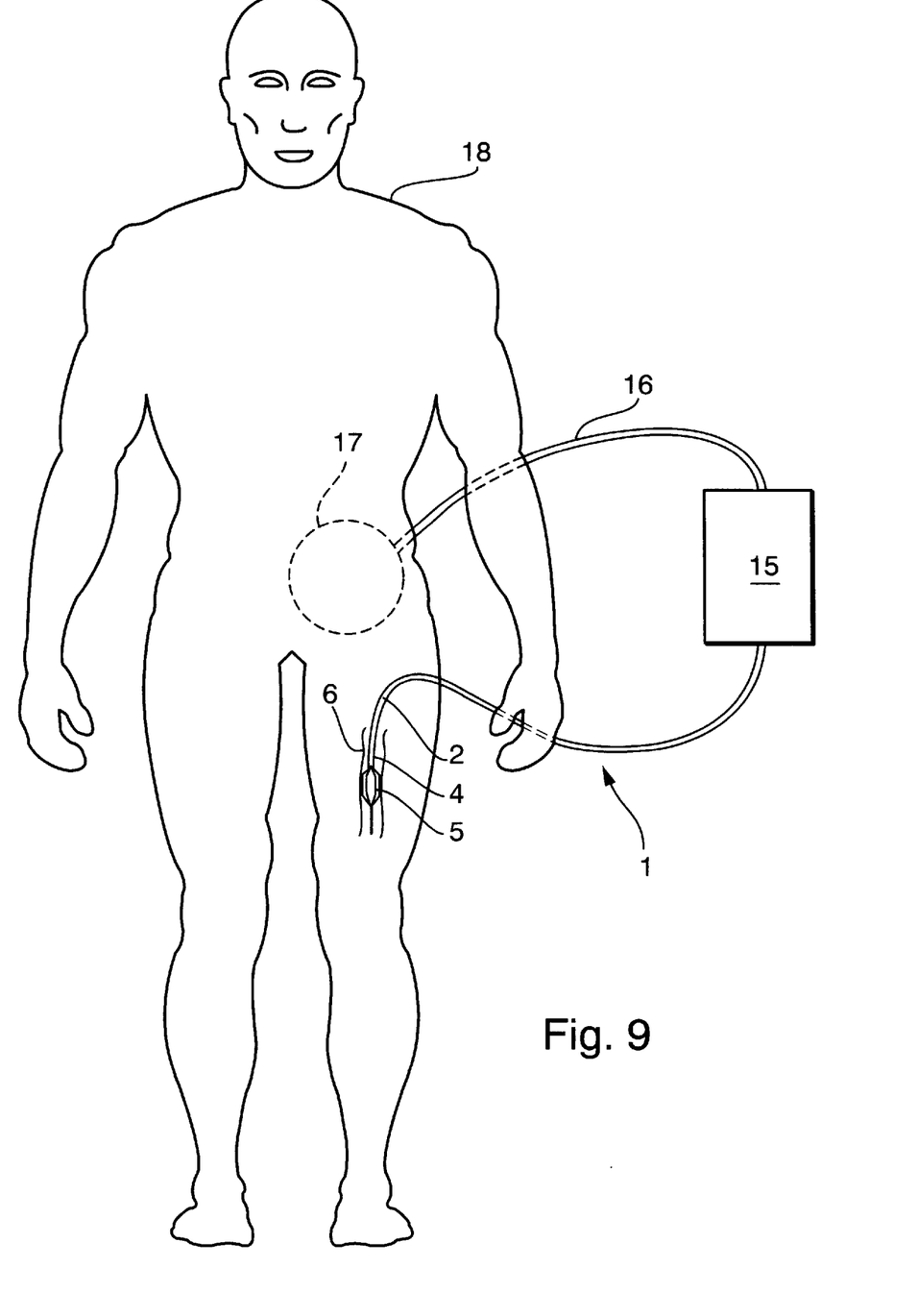
FIG. 9 is a schematic view of an animal body and of a catheter having its expander inserted into a blood vessel in one of the legs and with at least one expanding element of the expander connected to an energy source.

As shown in FIG. 9, the catheter 1 can be utilized in conjunction with a suitable energy source 15, particularly a source of high-frequency energy (such as a high-frequency heater of any known and suitable design). The source 15 can be connected to one, some or (preferably) all of the expanding elements 5a. For example, the connection between the energy source 15 and the expanding elements 5a can include the sleeve-like displacing member 12 and the tube 11 which latter is or can be connected to all of the elements 5a. FIG. 9 further shows a conductor 16 which connects the source 15 to a neutral pole 17. The pole 17 is in contact with the body of a patient 18 when the distal end 4 of the sheath 2 of the catheter 1 is introduced into a selected blood vessel 6 and the energy source 15 is to be put to use.

The expanding elements 5a can be designed and/or treated to ensure a satisfactory application of energy to the tissue surrounding a selected portion of an internal passage. For example, the elements 5a can be entirely or partially blank and the portions which are not blank can be provided with one or more coats of a suitable insulating material which prevents the treatment of the adjacent tisue by high-frequency or other energy.

In order to properly monitor the treatment of tissue with a selected energy (or to simply monitor the temperature of tissue in the absence of any thermal treatment), the improved catheter 1 is or can be provided with one or more suitable temperature monitoring devices 19 (hereinafter called thermometers) which can be connected with the source 15 (such as a high-frequency generator) and/or with a suitable control unit (not specifically shown) by one or more conductors 20 to furnish information pertaining to the temperature of the tissue at the central sections 5a' of the expanding elements 5a.

FIG. 8 shows a single thermometer 19 which is carried by a selected central section 5a' and is connected with a signal transmitting conductor 20. FIG. 7 shows four thermometers 19 each associated with a different central section 5a' and each connected with a discrete conductor 20; the thermometers 19 of FIG. 7 are staggered relative to each other in the longitudinal direction of the cage, i.e., in the longitudinal direction of the distal end 4 of the sheath 2.

It has been found that, at least in many instances, a single thermometer 19 suffices to furnish adequate information concerning the thermal treatment of the tissue surrounding the c-age of the exposed expander 5. For example, a single thermometer 19 can sample the temperature at any point along a selected stretch of an internal passage by causing the expander 5 to move longitudinally of as well as turn in such passage.

It is possible to provide at least one thermometer 19 (of any suitable compact design) on the section 5a' of each and every expanding element 5a. The conductor or conductors 20 can extend from the expander 5 to the proximal end 3 of the sheath 2 between the coaxial sleeve-like displacing members 12, 14 (see FIG. 5 which shows a total of six conductors 20, one for each of the expanding elements 5a). The conductors 20 alternate with the proximal terminals 7 of the expanding elements 5a.

The feature that, if the catheter 1 comprises two or more thermometers 19, such thermometers are staggered relative to each other in the longitudinal direction of the cage of the expander 5 is desirable and advantageous because a single turning of the expander 5 in a selected portion of the internal passage can suffice to furnish reliable information concerning the temperature of practically all portions of the surrounding tissue. Such thorough and reliable monitoring of the temperature can be achieved even if the axial (longitudinal) position of the expander 5 relative to the selected portion of the internal passage remains unchanged.

Instead of employing the displacing member 12 and/or 14 as a conductor between the tube 9 and the energy source 15, the space between the displacing members 12, 14 can accommodate one or more discrete conductors (in addition to the conductor or conductors 20) which connect the source 15 with one or more expanding elements 5a. Such confinement of the conductor(s) 20 and additional conductor(s) between the displacing members 12, 14 ensures a highly satisfactory shielding of the conductors.

The space between the proximal end portions of the displacing members 12, 14 is preferably sealed (in any suitable manner, not specifically shown in the drawings) to prevent the penetration of body fluids and/or other flowable substance or substances between the members 12, 14 and into contact with those portions of the conductors (such as 20) which extend from the expanding elements 5a to the proximal end 3 of the sheath 2.

The aforediscussed placing of the proximal terminals 7 and distal terminals 8 of the expanding elements 5a into two common planes which may but need not be parallel to each other and may but need not be normal to the axis of the distal end 4 is desirable and advantageous because this enhances the stability of the expander 5 without impairing its ability to expand and/or to contract. For example, an expander of such design can readily take up the reaction forces which are applied to the sections 5a' by the adjacent tissue upon expulsion of the expander from the distal end 4 of the sheath 2 and the resulting automatic development of an elongated cage of preferably cylindrical design. It can be said that each of the expanding elements 5a acts not unlike a bridge as soon as it is expelled from the distal end 4 of the sheath 2, and such bridges have been found to constitute highly satisfactory means for taking up the forces with which the surrounding tissue resists any expansion or further expansion of the respective portion of an internal passage.

Figure 10:
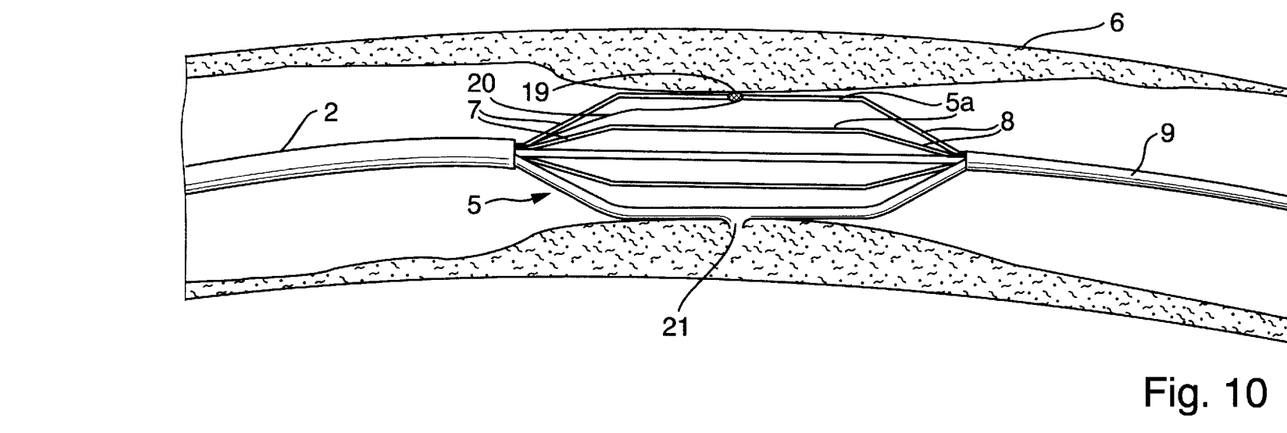
FIG. 10 is a view similar to that of FIG. 8 but showing a modified catheter wherein one of the expanding elements forming part of the expander is a conduit which delivers a flowable substance to a selected portion of the tissue surrounding a narrowed portion of a passage in a blood vessel or another part of an animal body.
Figure 11:
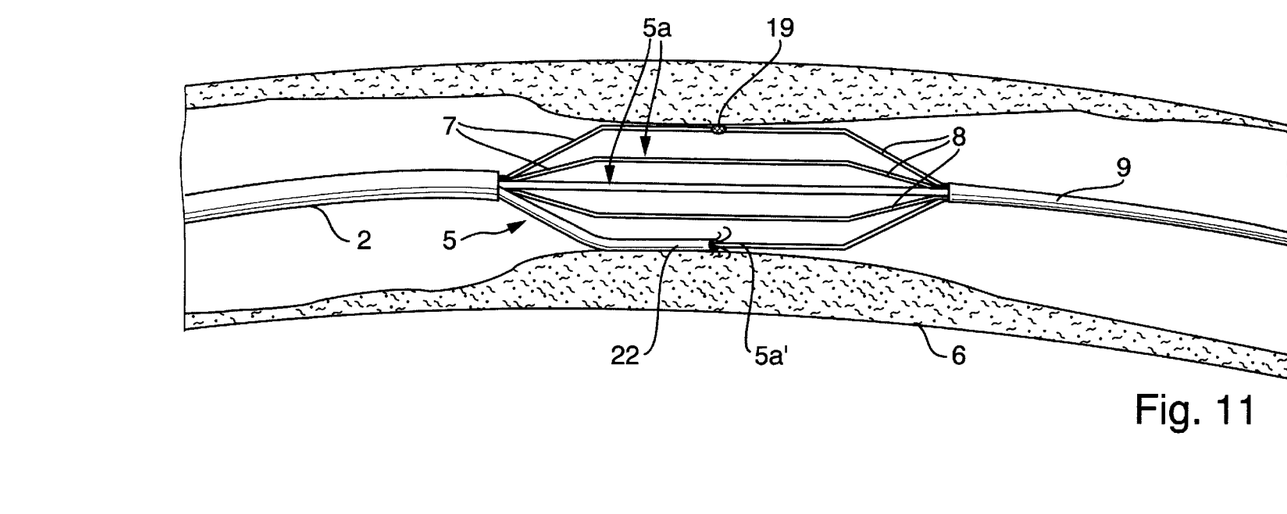
FIG. 11 is a view similar to that of FIG. 10 but showing a conduit which surrounds one of the expanding elements and discharges a flowable substance against tissue surrounding a selected portion of a passage in a blood vessel or another part of an animal body.

FIGS. 10 and 11 show that the improved catheter can further serve as a means for supplying one or more flowable substances (such as liquid medication(s)) to selected portions of the tissue surrounding an internal passage. FIG. 10 shows that one of the expanding elements constitutes a conduit having an outlet 21 which is preferably designed to direct one or more streams of a flowable substance substantially radially of and away from the axis of the cage of the expander so that the outflowing material impinges upon the adjacent tissue. FIG. 11 shows a modification wherein one of the expanding elements 5a is surrounded by a conduit 22 having a discharge end or outlet at the section 5a' of the respective element 5a to permit the outflow of a substance in one or more selected directions. The flowable substance can be a liquid or of pasty or any other consistency best suited for conveying in the conduit(s) of the type shown in FIGS. 10 and 11 and best suited to subject the tissue to a requisite treatment. For example, the flowable substance can be of a nature which prevents or reduces the likelihood of renewed or repeated stenosis.

It is clear that the conduit or expanding element having the outlet 21 shown in FIG. 10 must be connected to a suitable source of a flowable substance. For example, the tubular element including the outlet 21 can be extended (e.g., between the displacing members 12, 14) all the way to the proximal end 3 of the sheath 2.

The conduit 22 which is shown in FIG. 11 can be provided with two or more longitudinally spaced apart outlets which discharge metered quantities of a flowable substance into contact with the adjacent portions of the tissue.

It will be seen that the expander 5 of the improved catheter can serve a number of important purposes including mechanically expanding, propping or smoothing or massaging the surrounding tissue, supplying energy for thermal treatment of the surrounding tissue, supplying medications and/or other flowable substances to the tissue, and/or monitoring the temperature and/or other variable parameters of the tissue.

Since the elements 5a of the expander 5 are preferably designed to store at least some energy even when their sections 5a' bear upon the surrounding tissue, the cage of the expander 5 is not likely to collapse and the expander permits a body fluid (such as blood) to flow within that portion of an internal passage which contains the expander. Furthermore, and since the number of the expanding elements 5a is relatively small, and since these elements are preferably relatively thin or extremely thin wires or filaments, the flow restricting or impeding action of the expanded device 5 is not only acceptable but actually minimal.

The flexibility of the expanding elements 5a renders it possible to reliably and predictably expand or collapse the cage of the expander 5 in response to the exertion of a relatively small force.

The treatment of the tissue around a selected portion of an internal passage with energy supplied by the source 15 or another suitable energy source can be such that the temperature of the tissue is maintained within a range of somewhere between 37° C. and 100° C., i.e., such treatment can involve heating, pronounced heating or cooling of the tissue. The desired temperature can be maintained in response to signals furnished by the thermometer or thermometers 19 via conductor means 20. The application of a desired heating or cooling action can entail a smoothing or more satisfactory smoothing of the tissue, a coagulation of flowable substances or, if necessary, even a destruction of certain tissue. Such thermal treatment can but need not take place simultaneously with furnishing of one or more flowable substances in a manner as described in connection with FIGS. 10 and 11. It is also possible to thermally treat certain tissue and to simultaneously supply a flowable substance to other tissue around the exposed expander 5.

A presently preferred energy source 15 can constitute or include a 500-Khz high-frequency generator with an output of, for example, 50 watts. The thermometer or thermometers 19 can perform the additional function or functions of serving as sensor(s) for the controlled system of the source 15. Such thermometers 19 can transmit signals which are utilized to regulate the output of the source 15 in such a way that the temperature of the tissue being contacted by the heated or cooled element of elements 5a is always maintained at an optimum value or within an optimum range.

Another advantage of the expander 5 is that its relatively thin wire- or filament-like elements 5a do not offer a pronounced resistance to retraction into and/or expulsion from the distal end 4 of the sheath 2, even if the inner diameter of the distal end 4 is small or very small. This facilitates the introduction of the small-diameter distal end 4 into a selected portion of an internal passage, e.g., into a constricted portion of the type shown in FIGS. 8, 10 and 11.

Still another advantage of the improved dilatation catheter is its simplicity which is attributable, to a considerable extent, to the feature that the catheter need not embody any means for expanding the device 5, i.e., this device is simply designed to store energy during retraction into the distal end 4 of the sheath 2 and to expand as a result of the dissipation of some stored energy in automatic response to expulsion from the distal end 4.

The uniformity of the force which is being applied to the surrounding tissue by the sections 5a' of the preferably elongated and preferably cylindrical cage of the expanded (exposed) device 5 is attributable to the feature that the sections 5a' are elongated, parallel or at least nearly parallel to each other, and parallel or at least nearly parallel to the axis of the cage. Thus, portions of the sections 5a' need not bulge outwardly to subject the adjacent portions of the surrounding tissue to unpredictable and potentially excessive stresses while, at the same time, subjecting certain other portions of the surrounding tissue to insufficient radially outwardly directed forces (reference may be had again to the aforediscussed U.S. Pat. No. 3,557,794).

The absence of the need for discrete expanding means for the device 5 reduces the likelihood of pronounced obstruction of the flow of a body fluid through that portion of an internal passage which receives the expander 5.

The follower 9 exhibits the advantage that it facilitates the introduction of the distal end 4 of the sheath 2 into a selected portion of an internal passage by sliding along the guide 10 ahead of the distal end 4 of the sheath 2. In addition, the follower 9 maintains the distal terminals 8 of the expanding elements 5a in optimum positions relative to each other irrespective of the axial position of the expander 5 relative to the distal end 4, i.e., whether in the distal end 4 or in front of such distal end.

The tube 11 not only maintains the proximal terminals 7 of the expanding elements 5a in requisite (optimum) positions relative to each other but it also constitutes that part of the means for moving the expander 5 relative to the sheath 2 which establishes a connection with the sleeve-like displacing members 12 and 14. As mentioned hereinabove, the moving means 11–14 is preferably designed to move the expander 5 longitudinally of as well as to turn the expander relative to the distal end 4 of the sheath 2.

The axial passage of the tube 11 can serve for the reception of the guide 10 and, if necessary, for the reception of one or more additional component parts, e.g., electrical conductor means. This does not affect the mutual positions of the proximal terminals 7 which are preferably affixed to the exterior of the tube 11 (as shown in FIG. 4).

An advantage of the feature that the expanded device 5 can be turned (rotated) relative to the distal end 4 of the sheath 2 is that the tissue surrounding the cage of the exposed expander 5 can be smoothed, massaged and/or otherwise treated without it being necessary to rotate the entire catheter 1.

The handgrip portion or handgrip member 13 is or can be secured to the proximal end portion of at least one of the sleeve-like displacing members 12, 14 for the expander 5 in such a way that it can be manipulated for the purpose of moving the members 12, 14 longitudinally of and within the sheath 2 as well as to turn the members 12, 14 (and the expander 5) relative to the sheath.

Though the means for moving the expander 5 relative to the sheath 2 can comprise a single sleeve-like displacing member (12 or 14), the provision of two such members is often desirable and advantageous because this reduces the likelihood of undesirable deformation (such as twisting) of a single displacing member. Moreover, the means for moving the expander 5 out of the distal end 4 of the sheath 2 is much less likely to undergo deformation (such as upsetting in response to the development of excessive compressive stresses acting in a direction from the distal end 4 toward the proximal end 3) during expulsion of the expander 5 from the distal end 4.

The provision of a common hangrip portion or handgrip member 13 is desirable on the additional ground that this ensures full synchronization of movements of the displacing members 12, 14 relative to the sheath 2.

The strength of the cage which is defined by the elements 5a of the exposed expander 5 need not necessarily be affected (or need not be unduly affected) by the number of the elements 5a. Thus, if the number of the elements 5a is relatively small, they can be made of a relatively thick resilient wire-like or filamentary material, and the diameter of such material is or can be reduced accordingly if the number of the elements 5a is increased. As a rule, the cage will more closely resemble a cylinder if the number of the elements 5a is relatively large (e.g., ten).

As already mentioned above, the energy source 15 can be utilized for the treatment of each and every part of the tissue which contacts the elements 5a of the exposed expander 5, or for the treatment of selected portions of such tissue. All that is necessary is to simply insulate. selected elements 5a and/or selected portion(s) of one or more elements 5a, e.g., by applying thereto films or layers or other coatings of a suitable insulating material which prevents or reduces the effectiveness of thermal treatment attributable to or expected from the utilization of the energy source 15 or another suitable energy source. As also mentioned above, the thermal treatment can be selected in such a way that it entails a heating or a cooling or even a destruction of some of the tissue.

Those (intermediate) portions of the elements 5a which constitute the transitions between the end portions of the sections 5a' and the respective terminals 7, 8 can be normal to the axis of the cage (in the expanded condition of the device 5), or they can be inclined relative to such axis at oblique angles (see FIGS. 1, 6, 7, 8, 10 and 11). If the just mentioned intermediate portions of the elements 5a are normal to the axis of the cage, they are or they can be disposed in two parallel planes, namely in a first plane adjacent the proximal terminals 7 and in a second plane adjacent the distal terminals 8.

If only one of the expanding elements 5a is or includes a conduit with one or more outlets 21 (FIG. 10), or if only one of the elements 5a is surrounded by a conduit 22 (FIG. 11), such single conduit can serve to supply a flowable substance to any selected portion of the tissue surrounding an internal passage in response to angular and/or axial displacement of the cage of the exposed expander 5 relative to the (then) adjacent distal end 4 of the sheath 2. The flowable substance can be discharged at one or more locations in the region of the respective elongated straight section 5a' and/or in the region of the proximal terminal 7 and/or the distal terminal 8. An advantage of the embodiment which is shown in FIG. 11 is that the expanding element 5a which is surrounded by the conduit 22 can constitute a resilient wire, i.e., its ability to undergo temporary deformation and to reassume the shape shown in FIG. 11 remains unchanged even though a portion thereof is confined in the conduit 22. Moreover, the outlet or outlets of the conduit 22 can be readily placed at an optimum distance from the proximal terminals 7 and the distant terminals 8.

The improved catheter can be put to a number of different uses, for example, in the fields of cardiology and radiology. As shown in FIGS. 8 to 11, one of its presently preferred applications is to prevent excessive (or any) contraction, or renewed or repeated contraction of portions of internal passages in blood vessels or the like. For example, the improved dilatation catheter can be utilized to prevent spasmodic contraction of an artery in the course of a balloon angioplasty. Thus, the improved catheter can prevent excessive obstruction or total interruption of the flow of blood or another body fluid in an internal passage, such as a duct or a vessel. Moreover, in addition to preventing excessive contraction or total occlusion of an internal passage, the improved catheter can also serve to subject selected portions of tissue to one or more mechanical (such as smoothing and/or densifying) and/or thermal (such as heating or cooling or maintaining at a desired temperature) and/or other (contacting with one or more flowable medications and/or other flowable substances) treatments. For example, some and/or all of such treatments can be resorted to in order to reduce the likelihood of renewed stenosis.

If the improved catheter is equipped with high-frequency poles, it can be utilized to bring about a coagulation of selected portions of the tissue. The application of highly concentrated flowable substances to selected portions of tissue (as described with reference to FIGS. 10 and 11) can take place without resorting to injection procedures.

The resiliency (deformability) of the expander 5 (i.e., of its elements 5a) can be varied within a wide range by properly selecting the length, the number, the diameters and/or the material of the expanding elements. All this contributes to greater versatility of the improved catheter and to the convenience of its utilization in any one of a number of different fields.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of the above outlined contribution to the art of dilatation catheters and, therefore, such adaptations should and are intended to be comprehended within the meaning and range of equivalence of the appended claims.

What is claimed is:

1. A catheter for the treatment of tissue surrounding a passage in a portion of an animal body, comprising an elongated tubular sheath having a distal end adapted to be introduced into a selected portion of a passage; an expander including a plurality of at least partially resilient expanding elements together defining a cage contractible and expandible radially of said tubular sheath and having a contracted condition within and a radially expanded condition outside of the distal end of said sheath, said elements having spaced-apart distal and proximal terminals and elongated intermediate sections between the respective distal and proximal terminals said intermediate sections being at least substantially parallel to each other in said contracted as well as in said radially expanded condition of said cage, said elements being maintained in a stressed condition when located within said sheath and tending to expand radially outwardly beyond said distal end and to bear upon the tissue surrounding the selected portion of a passage when at least said intermediate section and said distal terminals are located outside of said distal end; and means for moving said elements within, beyond and back into the distal end of said sheath.

2. The catheter of claim 1, wherein said proximal and distal terminals respectively define first and second annular sections having at least substantially unchanging diameters, that portion of said cage which includes said intermediate sections having a diameter which exceeds said substantially unchanging diameters when said intermediate sections are located outside of said sheath, as a result of movement of said distal terminals and said intermediate sections beyond said distal end, to an extent determined by the extent of stress upon said elements when said intermediate sections are located within said sheath and upon the resistance offered by the tissue surrounding the selected portion of a passage when at least said distal terminal sand said intermediate sections are located outside and at the distal end of said sheath.

3. The catheter of claim 1, wherein each of said intermediate sections includes at least one wire-like filament.

4. The catheter of claim 3, wherein said intermediate sections are at least substantially straight and together constitute an elongated substantially tubular portion of said cage.

5. The catheter of claim 4, wherein said tubular portion of said cage at least resembles a hollow cylinder, at least when said intermediate sections and said distal terminals are located outside of said distal end.

6. The catheter of claim 1 wherein, at least when located outside of said distal end, said intermediate sections together form an elongated hollow cylindrical envelope having a longitudinal axis and a plurality of at least substantially straight wire-like components at least substantially parallel to said axis.

7. The catheter of claim 1, wherein said expander further includes a tubular follower connected with and extending beyond said distal terminals of said expanding elements away from said intermediate sections.

8. The catheter of claim 7, further comprising an elongated flexible guide surrounded by said sheath and said follower and having normally exposed proximal and distal end portions respectively adjacent said proximal end of said sheath and said follower.

9. The catheter of claim 1, wherein said moving means includes an elongated tube having a distal portion associated with the proximal terminals of said expanding elements and extending within an annulus defined by said proximal terminals toward said proximal end of said sheath.

10. The catheter of claim 9, wherein said tube contains a metallic material.

11. The catheter of claim 9, wherein said distal portion of said tube is secured to and maintains said proximal terminals in mutual positions such that said proximal terminals together form an annulus adjacent said intermediate sections.

12. The catheter of claim 11, wherein said distal portion of said tube is bonded to said proximal terminals.

13. The catheter of claim 9, wherein said distal portion of said tube has an external surface surrounded by the proximal terminals of said expanding elements.

14. The catheter of claim 1, wherein said tube has a proximal end portion extending beyond said proximal terminals toward said proximal end of said sheath and affixed to said displacing member.

15. The catheter of claim 1, wherein said moving means comprises an elongated displacing member disposed within said sheath and having a distal end portion at least indirectly affixed to the proximal terminals of said expanding elements.

16. The catheter of claim 15, wherein said displacing member is designed to push and pull said proximal terminals relative to said sheath.

17. The catheter of claim 15, wherein said moving means further comprises a handgrip portion affixed to a proximal end portion of said displacing member and accessible at the proximal end of said sheath to facilitate a longitudinal shifting of said displacing member and said proximal terminals relative to said sheath.

18. The catheter of claim 17, wherein said displacing member and said handgrip portion together constitute a means for imparting to said proximal terminals at least one of a plurality of movements including longitudinally and circumferentially of said sheath.

19. The catheter of claim 1, wherein said moving means comprises a first substantially sleeve-like displacing member disposed within said sheath and at least indirectly connected with the proximal terminals of said expanding elements, and a second substantially sleeve-like displacing member disposed within said sheath and at least indirectly connected with the proximal terminals of said expanding elements.

20. The catheter of claim 19, wherein one of said displacing members is surrounded by the other of said displacing members, said displacing members being jointly movable relative to said sheath at least in one of a plurality of different directions including longitudinally and circumferentially of said sheath.

21. The catheter of claim 19, wherein said moving means further comprises at least one handgrip member accessible at the proximal end of said sheath and connected to at least one of said displacing members.

22. The catheter of claim 21, wherein said at least one handgrip member is affixed to each of said displacing members and is movable relative to said proximal end at least in one of a plurality of directions including longitudinally and circumferentially of said sheath.

23. The catheter of claim 1, wherein said expander further comprises a tubular follower affixed to the distal terminals of said expanding elements and extending away from said intermediate sections, said moving means comprising at least one substantially sleeve-like displacing member affixed to at least one of said distal and proximal terminals, and further comprising an elongated flexible guide extending through said follower and said at least one displacing member, said guide on the one hand and said at least one displacing member and said follower on the other hand being movable relative to each other in at least one of the directions longitudinally and circumferentially of said sheath.

24. The catheter of claim 1, wherein said expander includes an array of between four and ten expanding elements.

25. The catheter of claim 1, wherein said expander comprises an array of six expanding elements.

26. The catheter of claim 1, wherein said expander comprises an array of between three and ten elongated expanding elements which are at least substantially equidistant from each other in a circumferential direction of said sheath.

27. The catheter of claim 1, further comprising a thermometer associated with at least one of said expanding elements.

28. The catheter of claim 27, wherein said thermometer is adjacent the intermediate section of the respective expanding element.

29. The catheter of claim 1, further comprising an energy source and means for connecting said source with at least one of said expanding elements.

30. The catheter of claim 29, wherein said source is a source of high-frequency energy and said means for connecting comprises a tubular conductor connected to at least some of said expanding elements.

31. The catheter of claim 1, further comprising a thermometer affixed to each of said expanding elements.

32. The catheter of claim 1 further comprising thermomemters connected to at least some of said expanding elements, said thermometers being staggered in the longitudinal direction of said sheath.

33. The catheter of claim 1, further comprising a thermometer disposed at least at one of said expanding elements, a source of energy, at least one first conductor arranged to connect said source with at least one of said expanding elements, and at least one second conductor connected with said thermometer, said moving means comprising first and second substantially sleeve-like displacing members affixed to the proximal terminals of said expanding elements and one of said displacing members being surrounded by the other of said displacing members, at least one of said conductors being located between said displacing members and extending from said expander toward said proximal end of said sheath.

34. The catheter of claim 1, wherein said distal terminals are disposed at least close to a first plane and said proximal terminals are disposed at least close to a second plane, at least one of said planes extending transversely of said sheath.

35. The catheter of claim 34, wherein said at least one plane is at least substantially normal to a longitudinal axis of said sheath.

36. The catheter of claim 34, wherein said at least one plane makes an oblique angle with a longitudinal axis of said sheath.

37. The catheter of claim 1, further comprising means for conveying a flowable substance from said proximal end of said sheath, within said sheath and to at least one of said expanding elements.

38. The catheter of claim 37, wherein said conveying means includes a portion forming part of said at least one expanding element.

39. The catheter of claim 37, wherein said at least one expanding element is a conduit for the flowable substance.

40. The catheter of claim 39, wherein said conduit has at least one outlet for flowable substance.

41. The catheter of claim 40, wherein said at least one outlet is arranged to discharge flowable substance substantially radially of and away from an elongated axis of said cage.

42. The catheter of claim 37, wherein said conveying means includes a conduit surrounding said at least one expanding element.

43. The catheter of claim 42, wherein said conduit has a discharge end for flowable substance at the intermediate section of the respective expanding element.

* * * * *

UNITED STATES PATENT AND TRADEMARK OFFICE
CERTIFICATE OF CORRECTION

| | | |
|---|---|---|
| PATENT NO. | : 5,954,742 | Page 1 of 1 |
| APPLICATION NO. | : 08/818574 | |
| DATED | : September 21, 1999 | |
| INVENTOR(S) | : Peter Osypka | |

It is certified that error appears in the above-identified patent and that said Letters Patent is hereby corrected as shown below:

In the Claims

In Claim 1 (col. 16, line 29), insert the text --, including an elongated tube having a distal portion associated with the proximal terminals of said expanding elements and an elongated flexible displacing member affixed to said tube and extending within and at least to the proximal end of said sheath-- after "sheath".

In Claim 9 (col. 17, line 3), change "moving means includes an" to --distal portion of said--; and lines 4-5, change "having a distal portion associated with the proximal terminals of said expanding elements and extending" to --extends--.

In Claims 10, 11 and 13 (col. 17, lines 8, 10 and 17), change the claim reference numeral "9", to --1--.

In Claim 15 (col. 17, lines 24-26), change "moving means comprises an elongated displacing member disposed within said sheath and having" to --displacing member has--.

In Claim 19 (col. 17, line 43), insert the text --further-- after "means"; and lines 44-47, cancel the text "a first substantially sleeve-like displacing member disposed within said sheath and at least indirectly connected with the proximal terminals of said expanding elements, and".

In Claim 23 (col. 18, lines 2-3), cancel the text "moving means comprising at least one substantially sleeve-like"; line 3, insert the text --being-- before "affixed"; line 6, cancel the text "at least one"; and line 7, cancel the text "at least one".

In Claim 33 (col. 18, line 45-46), change "comprising first and second substantially sleeve-like displacing members" to --further comprising a substantially sleeve-like second displacing member--.

Signed and Sealed this
Eleventh Day of February, 2014

Michelle K. Lee
*Deputy Director of the United States Patent and Trademark Office*